United States Patent [19]

Mestroni et al.

[11] Patent Number: 4,535,162
[45] Date of Patent: Aug. 13, 1985

[54] PROCESS FOR CATALYTICALLY REDUCING NITROAROMATIC COMPOUNDS

[75] Inventors: Giovanni Mestroni; Grazia Zassinovich, both of Trieste; Enzo Alessio, Gorizia, all of Italy

[73] Assignee: Montedison S.p.A., Milan, Italy

[21] Appl. No.: 504,748

[22] Filed: Jun. 16, 1983

[30] Foreign Application Priority Data

Jun. 21, 1982 [IT] Italy ................................ 21953 A/82

[51] Int. Cl.$^3$ .................. C07D 215/38; C07D 211/72; C07D 239/02
[52] U.S. Cl. ........................ 546/159; 260/465 E; 544/305; 546/171; 546/311; 546/88; 564/88; 564/305; 564/336; 549/68; 549/481
[58] Field of Search ................ 564/336, 305, 88; 546/88, 159, 311, 171; 260/465 E

[56] References Cited

U.S. PATENT DOCUMENTS

| | | | |
|---|---|---|---|
| 4,290,961 | 9/1981 | Mestroni et al. | 568/630 |
| 4,384,981 | 5/1983 | Dines et al. | 564/305 |
| 4,414,417 | 11/1983 | Mestroni et al. | 568/347 |

OTHER PUBLICATIONS

*Tetrahedron Letters,* No. 37, pp. 3385–3388, 1971.
*Journal of Molecular Catalysts* 12 (1981), pp. 385–387.

*Primary Examiner*—Donald G. Daus
*Assistant Examiner*—Cecilia Shen
*Attorney, Agent, or Firm*—Morgan, Finnegan, Pine, Foley & Lee

[57] ABSTRACT

A process is herein described for catalytically reducing nitroaromatic compounds by displacement of hydrogen from carbon monoxide and water or from synthesis gas to nitroaromatic compounds, the catalytic reduction being catalyzed by complexes of rhodium, iridium, ruthenium and osmium; said process is characterized in that the $CO+H_2O$ system or the $(CO+H_2)+H_2O$ system is caused to react with a nitroaromatic compound of formula:

$$Ar-(NO_2)_x \quad (I)$$

wherein Ar is an aryl or hetero-aryl group, also substituted by inert groups; x is an integer from 1 to 3, in the presence of a complex catalyst of formula:

$$[MChel(L)_2]^+ X^- \quad (II)$$

or of a catalyst composed by carbonyl compounds and chelants of formula:

$$M_z(CO)_y + nChel \quad (III)$$

wherein M=Rh, Ir, Ru, Os; "Chel" is a bidentate or tridentate aromatic nitrogen chelating compound; "L" is a molecule of carbon monoxide or of an olefin or half a molecule of a diolefin; $X^-$ is an anion selected from $Cl^-$, $Br^-$, $I^-$, $PF_6^-$, $BF_4^-$, $B(C_6H_5)_4^-$, $CO_3^{--}$ and $HCO_3^-$; z, y are integers with n being an integer or a fractional number, at temperatures ranging from about 25° C. to 250° C., at a carbon monoxide pressure between 1 and 150 atmospheres.

The products obtained from the hydrogenation of the starting nitroaromatic compounds consist of arylamines in general and are utilized as intermediates for the organic syntheses in the field of fine chemicals.

6 Claims, No Drawings

PROCESS FOR CATALYTICALLY REDUCING NITROAROMATIC COMPOUNDS

THE INVENTION

This invention relates to a process for catalytically reducing nitroaromatic compounds.

More particularly, the present invention relates to a catalytic process for reducing nitroaromatic compounds by displacement of hydrogen from carbon monoxide and water or from synthesis gas in the presence of complexes of rhodium, iridium, ruthenium, osmium.

The resulting compounds consist of arylamines in general.

The products obtained are usefully employable in a wide range of industrial appliances. In fact, they represent active intermediates for organic syntheses in general, with particular possibilities in the fine chemicals field. Among said products, aniline is utilized in the field of synthetic rubbers, in the production of isocyanates (polyurethanes), and especially, along with other arylamines preparable according to this invention, in the field relating to the dyestuff and intermediate industry, in the photographic, pharmaceutical products, in the plastic materials, propellants, insecticides and the like.

PRIOR ART BACKGROUND

Methods are known for catalytically reducing aromatic nitroderivatives by employing, as a hydrogenation source, both molecular hydrogen and hydrogen-donor, generally carbon monoxide and water, alcohols, etc.

In particular, there have been described methods of reducing aromatic nitroderivatives, e.g. nitrobenzene to aniline by displacement of hydrogen from the carbon monoxide and water system or from synthesis gas catalyzed by cluster or carbonyl compounds of Rh, Ir, Ru and Os such as, for example, $Rh_6(CO)_{16}$ in the presence of various amines such as trimethylamine, N,N-dimethylbenzylamine, pyridine, N-methylpyrrolidine, N,N,N',N'-tetramethylethylene diamine, paradimethylaminopyridine, out of which pyridine and N,N,N',N'-tetramethyl-ethylenediamine have proved to be the most active.

Amines are generally used at a concentration remarkably higher than the concentration of the substrate (aromatic nitroderivative).

A catalyst system has been now found, which is composed by complexes of Rh, Ir, Ru and Os in the presence of or containing bidentate or tridentate nitrogen aromatic chelants never used so far, which unexpectedly provide a catalytic activity by far higher than the hydrogen displacement catalyst of the art.

OBJECTS OF THE INVENTION

An object of the present invention is to provide a method of catalytically reducing nitroaromatic compounds to aromatic amines, with complexes of Rh, Ir, Ru and Os, in the presence or of containing aromatic, bidentate or tridentate nitrogen chelants, such method being simple, economic and particularly selective and especially direct to the obtainment of a high catalysis rate while employing the $CO+H_2O$ system or the $(CO+H_2)+H_2O$ system as a hydrogen-donor.

Other objects of the invention will be apparent from the discussion which follows:

GENERAL DESCRIPTION OF THE INVENTION

It has been found that the objects of the invention may be realized by providing a process for the catalytic reduction of nitroaromatic compounds by displacement of hydrogen from carbon monoxide and water or from synthesis gas to nitroaromatic compounds, said reduction being catalyzed by complexes of rhodium, iridium, ruthenium and osmium, such process being characterised in that the $CO+H_2O$ system or the $(CO+H_2)+H_2O$ system is made to react with a nitroaromatic compound of formula:

$$Ar-(NO_2)_x \qquad (I)$$

wherein Ar is an aryl group or a hetero-aryl group, also substituted by inert groups; X is an integer selected from 1 and 3, in the presence of a complex catalyst of formula:

$$[MChel(L)_2]^+X^- \qquad (II)$$

or of a catalyst composed by carbonyl compounds and chelants of formula:

$$M_z(CO)_y + nChel \qquad (III)$$

wherein M=Rh, Ir, Ru, Os; "Chel" represents a bidentate or tridentate aromatic nitrogen chelating compound; "L" represents a molecule of carbon monoxide or an olefin or half a molecule of a diolefin: $X^-$ is an anion selected from amongst $Cl^-$, $Br^-$, $I^-$, $PF_6^-$, $BF_4^-$, $B(C_6H_5)_4^-$, $CO_3^{--}$ and $HCO_3^-$, z, y represent integers, and n represents an integer or a fractional number, at temperatures ranging from about 25° C. to 250° C. and at a carbon monoxide pressure ranging from 1 to 150 atm.

As cited hereinabove, Ar represents in particular an aryl group or a hetero-aryl group, optionally condensed, having at least 5 atoms in the carbon ring (aryl groups), or optionally with hetero-atoms, selected from N, S and O) (hetero-aryl groups), such as, for example, the phenyl, naphthalene, anthracene, thienyl, furan, pyridine, quinoline groups.

Finally, the group Ar as defined hereinbefore may include also inert substituents in the reaction conditions, selected e.g. from the alkyl, alkoxide, aminic groups.

Thus, derivatives belonging to the classes of benzene, naphthalene, anthracene, thienyl, furan, pyridine, quinoline are employable as starting nitroaromatic derivatives.

The reaction is accomplished in solvents such as $H_2O$, ethanol, methanol, tetrahydrofuran, dioxane in admixture with water.

The hydrogen displacement reaction can be schematically represented by the following equation:

$$Ar-NO_2 + 3CO + H_2O \xrightarrow[\text{solv.}]{\text{cat}} Ar-NH_2 + 3CO_2$$

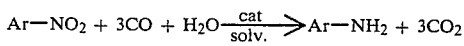

In general:

$$Ar(NO_2)_x + X(3CO) + XH_2O \xrightarrow[\text{solv.}]{\text{cat}} Ar(NH_2)_x + X(3CO_2).$$

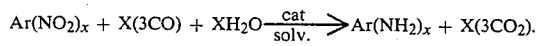

As regards the catalysts, the systems employed according to the invention have formulas (II) and (III) in which the aromatic bidentate or tridentate nitrogen chelant is preferably selected from 2,2'-bipyridyl(bipy), 4,4'-dimethyl-2,2' bipyridyl, 1,10-phenanthroline, 5,6-dimethyl-1,10-phenanthroline, 2,9-dimethyl-1,10-phenanthroline, 4,,7-dimethyl-1,10-phenanthroline, 3,4,7,8-tetramethyl-1,10-phenanthroline, 3,4,5,6,7,8,-hexamethylphenanthroline, 2,3,4,7,8,9-hexamethylphenanthroline, 2,4,7,9-tetramethylphenanthroline, sulphonated phenanthrolines, N,N,N',N'-ortho-phenylendiamine, N,N,N',N'-1,8-diaminonaphthalene and terpyridyl.

As catalysts according to the present invention it is possible to employ, for example:

[Rh, 3,4,7,8(CH$_3$)$_4$phen(CO)$_2$]B(C$_6$H$_5$)$_4$
[Rh4,7(CH$_3$)$_2$phen(CO)$_2$]B(C$_6$H$_5$)$_4$
[Rh phen(CO)$_2$]B(C$_6$H$_5$)$_4$
Rh$_6$(CO)$_{16}$+nChel(n=60).
Ru$_3$(CO)$_{12}$+3 (bipy), Ru$_3$(CO)$_{12}$+terpy
Ru$_3$(CO)$_{12}$+3(phen)
Ru$_3$(CO)$_{12}$+1,5phen
Ru$_3$(CO)$_{12}$+3(3,4,7,8(CH$_3$)$_4$phen).

wherein: "phen" means 1,10-phenanthroline, "bipy", means 2,2'-bipyridyl, "terpy" means terpyridyl.

Particularly effective have proved to be:

Rh$_6$(CO)$_{16}$+60(3,4,7,8(CH$_3$)$_4$phen) and
Ru$_3$(CO)$_{12}$+3phen
Ru$_3$(CO)$_{12}$+1,5phen The complexes employed as catalysts according to the present invention are prepared, in turn, by means of known and conventional techniques.

For example, the rhodium complex of formula:

[Rh3,4,7,8(CH$_3$)$_4$phen(CO)$_2$]B(C$_6$H$_5$)$_4$ is preparable starting from:

[Rh3,4,7,8(CH$_3$)$_4$phen COD]B(C$_6$H$_5$)$_4$;
(COD=1,5-cyclooctadiene) by treatment with
carbon monoxide in methanol at room temperature
and pressure.

The carboyl clusters are prepared too according to conventional techniques.

The catalyst is employed, according to the invention, in amounts which may range over a wide range.

Advantageous results are obtained by using, for each mole of nitroaromatic compound, amounts ranging from $1\times10^{-2}$ to $1\times10^{-5}$ grams atoms of metal contained in the catalyst.

Suitable reaction mediums are ethanol—H$_2$O (5%), tetrahydrofuran-water.

The reducing reaction according to the invention is accomplished at carbon monoxide pressures ranging from the atmospheric pressure and 150 atmospheres.

Temperatures in the range of from 25° C. to about 200° C. are possible.

Reducible nitroaromatic compounds according to the present invention are, in particular, among the aromatics, nitrobenzene, nitrotoluene, nitroanisole, nitrochlorobenzene, nitrobenzonitrile, nitronaphthalene, dinitrobenzene, dinitrotoluene, dinitroaniline, dinitrobenzamide; among the heteroaromatics, the nitropyridines, nitroquinolines, etc.

The product is then separated according to conventional techniques. In practice, it is a matter of separating the solvent, if any, by distillation, while the high boiling portion consists of the compound generally quantitatively hydrogenated.

In particular, the catalyst can be removed from the reaction medium by adsorption on an animal charcoal, ion-exchange resins (in particular in the case of the sulphonated phenanthrolines).

According to an effective embodiment, it is practically operated as follows:

A solution containing the catalyst and the nitroaromatic compound is introduced, in a carbon monoxide atmosphere, into a reactor equipped with feeding systems for the reagents, thermoregulated and magnetically stirred. The desired amount of carbon monoxide under pressure is then introduced, whereupon it is heated to the prefixed temperature and for the prefixed period of time. At the conclusion of the reaction, which is controlled, for example, by gaschromatography, the product is isolated according to conventional techniques.

The process according to the present invention permits to obtain, thanks to a catayst' activity by far higher than the one of the hydrogen displacement catalysts of the art, high conversion yields exceeding 98% in shorter times, employing chelant concentrations which are considerably lower than the concentrations of the substrate and with a high substrate/catalyst ratio.

The process according to the present invention, as it operates in the absence of co-catalysts, which are usually employed in the art, permits an easier isolation of the reaction products.

SPECIFIC DESCRIPTION OF THE INVENTION

The invention will now be further described in the following examples, which are given, however, for merely illustrative purposes, examples 43 through 52 being given by way of comparison with the processes of the art.

The symbols employed in the examples are:
"bipy", which means 2,2'-bipyridyl,
"phen", which means 1-10-phenanthroline,
S—substrate,
"chel", which means a chelating compound as is defined in the description;
the ratios are expressed in moles.

EXAMPLE 1

To 50 ml of ethanol—H$_2$O (5%) there were added 0.615 g ($5\times10^{-3}$ moles) of nitrobenzene and then $5\times10^{-3}$ m.moles of [Rh3,4,7,8(CH$_3$)$_4$phen(CO)$_2$]B(C$_6$H$_5$)$_4$. The resulting solution was poured into a 100 ml autoclave.

The autoclave was charged with 30 atmospheres of carbon monoxide at room temperature and successively it was heated to 165° C. The reaction trend was checked by means of gaschromatography taking samples at intervals. After 2 hours, aniline was obtained with a yield of 43% with respect to the starting nitrobenzene.

Ratios: S/Rh=1,000; chel/Rh=1.

EXAMPLE 2

To 50 ml of ethanol—H$_2$O (5%) there were added 0.615 g ($5\times10^{-3}$ moles) of nitrobenzene and then $5\times10^{-3}$ m.moles (1.18 mg) of 3,4,7,8(CH$_3$)$_4$phen.

The solution so obtained was poured into a 100 ml autoclave containing $0.83\times10^{-3}$ m.moles (0.88 mg) of Rh$_6$(CO)$_{16}$.

The autoclave was charged with 30 atmospheres of carbon monoxide at room temperature and successively it was heated to 165° C.

After 2 hours, aniline was obtained with a yield of 43% with respect to the starting nitrobenzene.

Ratios: S/Rh=1,000; chel/Rh=1.

EXAMPLE 3

To 50 ml of ethanol—H$_2$O (5%) there were added 0.615 g (5×10$^{-3}$ moles) of nitrobenzene, then 3.75 mg (5×10$^{-3}$ m.moles) of [Rh3,4,7,8(CH$_3$)$_4$phen(-CO)$_2$]B(C$_6$H$_5$)$_4$ and finally 3.54 mg (1.5×10$^{-2}$ m.moles) of 3,4,7,8-(CH$_3$)$_4$phen. The resulting solution was poured into a 100 ml autoclave. The autoclave was charged with 30 atmospheres of carbon monoxide at room temperature and successively it was heated to 165° C.

After 2 hours, aniline was obtained with a yield of 96% in respect of the starting nitrobenzene.

Ratios: S/Rh=1,000; chel/Rh=4.

EXAMPLE 4

To 50 ml of ethanol/H$_2$O (5%) there were added 0.615 g (5×10$^{-3}$ moles) of nitrobenzene and successively 4.72 mg of 3,4,7,8-(CH$_3$)$_4$phen. The solution so obtained was poured into a 100 ml autoclave containing 0.88 mg (0.83×10$^{-3}$ m.moles) of Rh$_6$(CO)$_{16}$. 30 atmospheres of carbon monoxide ar room temperature were charged into the autoclave, which was then heated to 165° C. After 2 hours, aniline was obtained with a yield of 96% in respect of the starting nitrobenzene.

Ratios: S/Rh=1,000; chel/Rh=4.

EXAMPLE 5

It was operated as in Example 1, while employing 2.36 mg of 3,4,7,8-(CH$_3$)$_4$phen.

After 2 hours, aniline was obtained with a yield of 62%.

Ratios: S/Rh=1,000; chel/Rh=2.

EXAMPLE 6

It was operated as in Example 4, while employing 11.8 mg of 3,4,7,8-(CH$_3$)$_4$phen.

After 2 hours, aniline was obtained with a yield of 100%.

Ratios: S/Rh=1,000; chel/Rh=10.

EXAMPLE 7

It was operated as in example 2, while employing 0.78 mg (5×10$^{-3}$ m.moles) of bipy.

After 2 hours, aniline was obtained with a yield of 0.82% referred to the starting nitrobenzene.

Ratios: S/Rh=1,000; chel/Rh=1.

EXAMPLE 8

It was operated as in example 2, while employing 0.96 mg (5×10$^{-3}$ m.moles) of phen.

After 2 hours, aniline was obtained with a yield of 7.5% in respect of the starting nitrobenzene.

Ratios: S/Rh=1,000; chel/Rh=1.

EXAMPLE 9

It was operated like in example 2, while employing 9.6 mg (5×10$^{-2}$ m.moles) of phen.

After 2 hours, aniline was obtained with a yield of 54% calculated on the starting nitrobenzene.

After 3 hours, aniline was obtained with a yield of 91% calculated on the starting nitrobenzene.

Ratios: S/Rh=1,000; chel/Rh=10.

EXAMPLE 10

It was operated like in example 2, while employing 1.04 mg (5×10$^{-3}$ moles) of 4,7(CH$_3$)$_2$phen.

After 2 hours, aniline was obtained with a yield of 25% with respect to the starting nitrobenzene.

Ratios: S/Rh=1,000; chel/Rh=1.

EXAMPLE 11

It was operated like in example 2, while employing 4.16 mg (2×10$^{-2}$ m.moles) of 4,7(CH$_3$)$_2$phen.

After 2 hours, aniline was obtained with a yield of 64.5% with respect to the starting nitrobenzene.

Ratios: S/Rh=1,000; chel/Rh=4.

EXAMPLE 12

It was obtained like in example 2, while employing 1.80 mg (5×10$^{-3}$ m.moles) of 2.9(CH$_3$)$_2$4,7(C$_6$H$_5$)$_2$phen.

After 2 hours, aniline was obtained with a yield of 4.5% with respect to the starting nitrobenzene.

Ratios: S/Rh=1,000; chel/Rh=1.

EXAMPLE 13

It was operated like in example 2, while employing 10.73 mg (2×10$^{-2}$ m.moles) of sulphonated phen of formula:

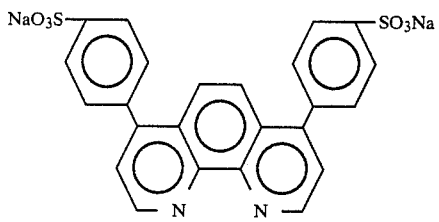

After 2 hours, 45.5% of aniline, referred to the starting nitrobenzene, was obtained.

Ratios: S/Rh=1,000; chel/Rh=4.

EXAMPLE 14

It was operated as in example 13, while employing ethanol—H$_2$O (10%).

After 2 hours, aniline was obtained with a yield of 59.5% referred to the starting nitrobenzene.

Ratios: S/Rh=1,000; chel/Rh=4.

EXAMPLE 15

It was operated like in example 14, while employing 2.68 mg (5×10$^{-3}$ m.moles) of sulphonated phen.

After 2 hours, 20% of aniline calculated on the starting nitrobenzene was obtained.

Ratios: S/Rh=1,000; chel/Rh=1.

EXAMPLE 16

It was operated like in example 14, while employing 11.33 mg (2×10$^{-2}$ m.moles) of 2,9 dm sulphonated phen of formula

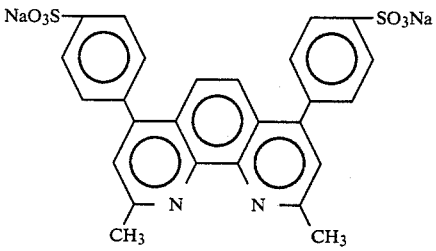

After 2 hours, aniline was obtained with a yield of 7% calculated on the starting nitrobenzene.

Ratios: S/Rh=1000; chel/Rh=4.

EXAMPLE 17

To 50 ml of ethanol—$H_2O$ (5%) there were added 0.615 g ($5\times10^{-3}$ moles) of nitrobenzene and then 0.96 mg ($5\times10^{-3}$ m.moles) of phen.

The resulting solution was poured into a 100 ml autoclave containing 1.06 mg ($1.6\times10^{-3}$ m.moles) of $Ru_3(CO)_{12}$. 30 atmospheres of carbon monoxide at room temperature were charged into the autoclave, which was then heated to 165° C.

After 2 hours, aniline was obtained with a yield higher than 98% referred to the starting nitrobenzene.

Ratios: S/Ru=1,000; chel/Ru=1.

EXAMPLE 18

It was operated like in example 17, while employing 0.48 mg ($2.5\times10^{-3}$ moles) of 1,10-phenanthroline.

After 2 hours, aniline was obtained with a yield higher than 98% referred to the starting nitrobenzene.

Ratios: S/Ru=1,000; chel/Ru=0.5.

EXAMPLE 19

It was operated like in example 17, while employing 1.18 mg ($5\times10^{-3}$ m.moles) of 3,4,7,8-$(CH_3)_4$phen.

After 2 hours, aniline was obtained with a yield higher than 97% calculated on the starting nitrobenzene.

Ratios: S/Ru=1,000; chel/Ru=1.

EXAMPLE 20

It was operated like in example 17, while employing 1.92 mg ($1\times10^{-2}$ m.moles) of phen.

After 2 hours, aniline was obtained with a yield of 56.5% referred to the starting nitrobenzene.

Ratios: S/Ru=1,000; chel/Ru=2.

EXAMPLE 21

It was operated like in example 17, while employing 0.78 mg ($5\times10^{-3}$ m.moles) of bipy.

After 2 hours, aniline was obtained with a yield of 79% in respect of the starting nitrobenzene.

Ratios: S/Ru=1,000; chel/Ru=1.

EXAMPLE 22

It was operated like in example 17, while employing 0.685 g ($5\times10^{-3}$ moles) of paranitrotoluene.

After 2 hours, paratoluidine was obtained with a yield of 98.5% referred to the starting paranitrotoluene.

Ratios: S/Ru=1,000; chel/Ru=1.

EXAMPLE 23

It was operated like in example 17, while employing 0.765 g ($5\times10^{-3}$ moles) of paranitroanisole.

After 2 hours, paramethoxyaniline was obtained with a yield of 66% on the starting paranitroanisole.

Ratios: S/Ru=1,000; chel/Ru=1.

EXAMPLE 24

It was operated like in example 17, while employing 0.787 g of p-chloronitrobenzene ($5\times10^{-3}$ moles).

After 2 hours, p-chloroaniline was obtained with a yield of 7% on the starting nitroderivative.

Ratios: S/Ru=1,000; chel/Ru=1.

EXAMPLE 25

It was operated like in example 17, while employing 0.910 g ($5\times10^{-3}$ moles) of 2,4-dinitro-toluene and 3.84 mg ($2\times\times10^{-2}$ m.moles) of phen as well as 4.24 mg ($6.67\times10^{-3}$ m.moles) of $Ru_3(CO)_{12}$.

After 15 hours, 2,4-diamino-toluene was obtained with a yield of 77% with respect to the starting 2,4-dinitro-toluene.

Ratios: S/Ru=250; chel/Ru=1.

EXAMPLE 26

It was operated like in example 17, while employing 1.92 mg of phen ($1\times10^{-2}$ m.moles) and 2.12 mg ($3.34\times10^{-3}$ m.moles) of $Ru_3(CO)_{12}$.

After 90 minutes, aniline was obtained with a yield higher than 98% referred to the starting nitrobenzene.

Ratios: S/Ru=500; chel/Ru=1.

EXAMPLE 27

It was operated like in example 17, while employing 3.84 mg of phen ($2\times10^{-2}$ m.moles) and 4.24 mg ($6.64\times10^{-3}$ m.moles) of $Ru_3(CO)_{12}$.

After 60 minutes, aniline was obtained with a yield of 98% with respect to the starting nitrobenzene.

Ratios: S/Ru=250; chel/Ru=1.

EXAMPLE 28

It was operated like in example 27, while working at a temperature of 125° C.

After 4 hours, aniline with a 96% yield with respect to the starting nitrobenzene was obtained.

Ratios: S/Ru=250; chel/Ru=1.

EXAMPLE 29

It was operated like in example 27, while working at 90° C. After 4 hours, aniline with a 10.5% yield with respect to the starting nitrobenzene was obtained.

Ratios: S/Ru=250; chel/Ru=1.

EXAMPLE 30

It was operated like in example 27, at a temperature of 50° C. After 17 hours, aniline with a 0.5% yield with respect to the starting nitrobenzene was obtained.

Ratios: S/Ru=250; chel/Ru=1.

EXAMPLE 31

It was operated like in example 17, while employing a carbon monoxide pressure of 50 atmospheres (at room temperature). After 2 hours, aniline with a 98% yield referred to the starting nitrobenzene was obtained.

Ratios: S/Ru=1,000; chel/Ru=1.

EXAMPLE 32

It was operated like in example 17, while employing 10 atmospheres of carbon monoxide (at room temperature).

After 2 hours, aniline with a 90% yield with respect to the starting nitrobenzene was obtained.

Ratios: S/Ru=1,000; chel/Ru=1.

EXAMPLE 33

It was operated like in example 17, while employing 5 atmospheres of carbon monoxide (at room temperature). After 16 hours, aniline with a 90% yield in respect of the starting nitrobenzene was obtained.

Ratios: S/Ru=1,000; chel/Ru=1.

EXAMPLE 34

It was operated like in example 17, while employing 1.23 g ($1 \times 10^{-2}$ moles) of nitrobenzene and a CO pressure of 50 atmospheres. After 2 hours, aniline with a 93% yield in respect of the starting nitrobenzene was obtained.

Ratios: S/Ru=2,000; chel/Ru=1.

EXAMPLE 35

It was operated like in example 17, while employing 2.46 g ($2 \times 10^{-2}$ moles) of nitrobenzene and a CO pressure of 50 atmospheres. After 4 hours, aniline with a 35.5% yield with respect to the starting nitrobenzene was obtained.

Ratios: S/Ru=4,000; chel/Ru=1.

EXAMPLE 36

It was operated like in example 28, while employing 0.38 mg of phen. After 2 hours, aniline with a yield of 25.6%, referred to the starting nitrobenzene, was obtained.

Ratios: S/Ru=250; chel/Ru=0.1.

EXAMPLE 37

It was operated like in example 28, while employing 0.47 mg of $3,4,7,8(CH_3)_4$phen.

After 2 hours, aniline with a yield of 21.3%, referred to the starting nitrobenzene, was obtained.

Ratios: S/Ru=250; chel/Ru=1.

EXAMPLE 38

It was operated like in example 28, while employing 12.48 mg of $2,9(CH_3)_2$phen.

After 3 hours, aniline with a 90% yield in respect of the starting nitrobenzene was obtained.

Ratios: S/Ru=250; chel/Ru=3.

EXAMPLE 39

To 50 ml of ethanol—$H_2O$ (5%) there were additioned: 0.615 g ($5 \times 10^{-3}$ moles) of nitrobenzene and, successively, 4.02 mg of $[Ir3,4,7,8Me_4phen(CO)_2]B(C_6H_5)_4$.

The solution so obtained was poured into a 100-ml autoclave. Into the autoclave, 30 atmospheres of carbon monoxide were charged at room temperature, whereafter it was heated to 165° C. After 2 hours, aniline with a 1.3% yield referred to the starting nitrobenzene was obtained.

Ratio: S/Ir=1,000.

EXAMPLE 40

It was operated like in example 17, while employing 1.5 mg of $Os_3(CO)_{12}$. After 2 hours, aniline with a yield of 1%, with respect to the starting nitrobenzene, was obtained.

Ratios: S/Os=1,000; chel/Os=1.

EXAMPLE 41

It was operated like in example 2, while employing 1.16 mg of terpyridyl ($5 \times 10^{-3}$ m.moles).

After 2 hours, aniline was obtained with a yield of 4.5% calculated on the starting nitrobenzene.

Ratios: S/Rh=1,000; chel/Rh=1.

EXAMPLE 42

It was operated like in example 17, while employing 1.16 mg of terpyridyl ($5 \times 10^{-3}$ m.moles).

After 2 hours, aniline with a yield of 90%, referred to the starting nitrobenzene, was obtained.

Ratios: S/Ru=1,000; chel/Ru=1.

EXAMPLES 43–46 (comparative tests)

A set of 4 nitrobenzole reduction tests was carried out under the same conditions as in example 2, one of such tests not employing $3,4,7,8-(CH_3)_4$phen and the other three tests employing, instead of $3,4,7,8-(CH_3)_4$phen, different amounts of pyridine, which is one of the amines capable of imparting, according to the art, the highest catalytic activity. The reaction conditions employed for the synthesis were as follows: catalyst $Rh_6(CO)_{16} \pm$ amines; T=165° C.; CO pressure=30 atmospheres; [Rh]=$1 \times 10^{-4}$ moles; S/Rh=1,000; solvent=ethanol—$H_2O$ (5%).

The various amounts of pyridine employed and the results obtained are recorded on Table I in comparison with example 2 of the present invention.

TABLE I

| Example No. | Amine | Amine/Rh | % Conversion (2 hours) |
|---|---|---|---|
| 43 | — | — | 0 |
| 44 | pyridine | 2 | 0 |
| 45 | pyridine | 200 | traces |
| 46 | pyridine | 2000 | 2.4 |
| 2 | $3,4,7,8-(CH_3)_4$phen | 1 | 43 |

EXAMPLES 47–49 (comparative tests)

A series of 3 nitrobenzole reduction tests was carried out under the same reaction conditions as in examples 43–46, using the $Rh_6(CO)_{16}$+amine catalytic system, and employing, as an amine, N,N,N',N'-tetramethylethylene diamine in different amounts, said amine being capable of imparting, according to the prior art, the highest catalytic activity.

The employed diamine amounts and the results obtained are recorded on Table II in comparison with example 5 of the present invention.

TABLE II

| Example No. | Amine | Amine/Rh | % Conversion (2 hours) |
|---|---|---|---|
| 47 | N,N,N',N'—tetramethylethylene diamine | 10 | 6.5 |
| 48 | N,N,N',N'—tetramethylethylene diamine | 100 | 26.6 |
| 49 | N,N,N',N'—tetramethylethylene diamine | 500 | 56.3 |
| 5 | $3,4,7,8-(CH_3)_4$ phen | 2 | 62 |

EXAMPLES 50–52 (comparative tests)

Nitrobenzole to aniline reduction tests were carried out with the CO+$H_2O$ system, under the same reaction conditions of examples 43–46, by employing the $Ru_3(CO)_{12}$ catalytic system in the absence and in the presence of various amounts of pyridine.

The obtained results are recorded on Table III in comparison with examples 17, 18 and 19 of the present invention.

TABLE III

| Example No. | Amine | Amine/Ru | % Conversion (2 hours) |
|---|---|---|---|
| 50 | — | — | 8 |
| 51 | pyridine | 2 | 9.3 |

TABLE III-continued

| Example No. | Amine | Amine/Ru | % Conversion (2 hours) |
|---|---|---|---|
| 52 | pyridine | 20 | 10 |
| 17 | 1,10-phenanthroline | 1 | 98 |
| 18 | 1,10-phenanthroline | 0.5 | 98 |
| 19 | 3,4,7,8(CH$_3$)$_4$phen | 1 | 97 |

What is claimed is:

1. A process for catalytically reducing nitroaromatic compounds by displacement of hydrogen from carbon monoxide and water or from synthesis gas to nitroaromatic compounds, such reduction being catalyzed by complexes of rhodium, iridium, ruthenium and osmium; characterized in that the CO+H$_2$O system or the (CO+H$_2$)+H$_2$O system is reacted with a nitroaromatic compound of formula;

$$Ar-(NO_2)_x \qquad (I)$$

wherein Ar is an aryl group or a hetero-aryl group, optionally substituted by inert groups; x is an integer selected from 1 to 3, in the presence of a complex catalyst having the formula:

$$[MChel(L)_2]^+ X^- \qquad (II)$$

or of a catalyst composed by carbonyl compounds and chelants of formula:

$$M_z(CO)_y + nChel \qquad (III)$$

wherein M=Rh, Ir, Ru, Os; "Chel" is a chelating bidentate or tridentate aromatic nitrogen compound selected from the group consisting of 2,2'-dipyridyl, 4,4'-dimethyl-2,2'dipyridyl, 1,10-phenanthroline, 5,6-dimethyl-1,10-phenanthroline, 2,9-dimethyl-1,10-phenanthroline, 4,7-dimethyl1,10-phenanthroline, 3,4,7,8-tetra-methyl-1,10-phenanthroline, 3,4,5,6,7,8-hexamethyl-phenanthroline, 2,3,4,7,8,9-hexamethyl-phenanthroline, 2,4,7,9-tetramethylphenanthroline, sulphonated phenanthrolines, N,N,N'N'-ortho-phenylene diamine and N,N,N',N'-ortho-phenylene diamine and N,N,N',N'-1,8-diaminonaphthalene and terpyridyl; "L" is a molecule of carbon monoxide or of an olefin or half a molecule of a diolefin; X$^-$ is an anion selected from Cl$^-$, Br$^-$, I$^-$, PF$_6$$^-$, BF$_4$$^-$, (B(C$_6$H$_5$)$_4$, $^-$CO$_3$$^{--}$ and HCO$_3$$^-$; z and y, are integers and n is an integer or a fractional number, at temperatures ranging from about 25° C. to 250° C., at a carbon monoxide pressure ranging from 1 to 150 atmospheres.

2. The process according to claim 1, characterized in that the nitroaromatic compound of formula (1) is selected from the derivatives of the class of benzene, naphthalene, anthracene, thienyl, furan, pyridine and quinoline, optionally substituted by inert groups, under the reaction conditions, such as the alkyl, alkoxyl, aminic groups and the like.

3. The process according to claim 1, characterized in that it is carried out in a medium selected from amongst water, ethanol, methanol, tetrahydrofuran, dioxane in admixture with water.

4. The process according to claim 1, characterized in that for 1 mole of nitroaromatic compound (I) there are employed from 1×10$^{-2}$ to 1×10$^{-5}$ grams atoms of metal contained in the catalyst.

5. The process according to claim 1, characterized in that the nitroaromatic compound (I) is selected from nitrobenzene, nitrotoluene, nitroanisole, nitrochlorobenzene, nitroaniline, nitrobenzoamide, nitrobenzonitrile, nitronaphthalene, dinitrobenzene, dinitrotoluene, dinitroaniline, dinitrobenzoamide, nitropyridine, nitroquinoline.

6. The process according to claim 1, characterized in that the catalyst of formula (II) or (III) is selected from amongst:

[Rh3,4,7,8(CH$_3$)$_4$phen(CO)$_2$]B(C$_6$H$_5$)$_4$,
[Rh4,7(CH$_3$)$_2$phen(CO)$_2$]B(C$_6$H$_5$)$_4$,
[Rh phen(CO)$_2$]B(C$_6$H$_5$)$_4$,
Rh$_6$(CO)$_{16}$+60Chel,
Rh$_6$(CO)$_{16}$+60[3,4,7,8(CH$_3$)$_4$phen]
Ru$_3$(CO)$_{12}$+3bipy, Ru$_3$(C))$_{12}$+terpyridyl,
Ru$_3$(CO)$_{12}$+3phen, Ru$_3$(CO)$_{12}$+1,5phen,
Ru$_3$(CO)$_{12}$+3[3,4,7,8(CH$_3$)$_4$phen]
 wherein "phen" means phenanthroline, "Chel" has the meaning as defined in claims 1 and 4, "bipy" means 2,2'-dipyridyl.

* * * * *